(12) United States Patent
Berger et al.

(10) Patent No.: US 8,705,803 B2
(45) Date of Patent: Apr. 22, 2014

(54) METHOD FOR EVALUATING TIRE SELF-CLEANING CAPABILITY BY ANALYZING RECORDED IMAGES

(75) Inventors: Phillip A. Berger, Simpsonville, SC (US); Michael Arant, Williamston, SC (US)

(73) Assignees: Compagnie Generale des Etablissements Michelin, Clermont-Ferrand (FR); Michelin Recherche et Technique S.A., Granges-Paccott (CH)

( * ) Notice: Subject to any disclaimer, the term of this patent is extended or adjusted under 35 U.S.C. 154(b) by 66 days.

(21) Appl. No.: 13/511,728

(22) PCT Filed: Nov. 25, 2009

(86) PCT No.: PCT/US2009/065853
§ 371 (c)(1),
(2), (4) Date: May 24, 2012

(87) PCT Pub. No.: WO2011/065944
PCT Pub. Date: Jun. 3, 2011

(65) Prior Publication Data
US 2012/0263354 A1    Oct. 18, 2012

(51) Int. Cl.
*G06K 9/00*    (2006.01)
(52) U.S. Cl.
USPC .......................................................... 382/107
(58) Field of Classification Search
None
See application file for complete search history.

(56) References Cited

U.S. PATENT DOCUMENTS

| | | | |
|---|---|---|---|
| 3,030,998 | A | 2/1960 | Jensen |
| 3,817,306 | A | 6/1974 | Sidles |

(Continued)

FOREIGN PATENT DOCUMENTS

| | | | |
|---|---|---|---|
| EP | 0 837 308 A2 | | 4/1998 |
| WO | WO 2005/018957 | * | 3/2005 |
| WO | WO 2005 018957 A2 | | 3/2005 |

OTHER PUBLICATIONS

European Search Report for EP0837308A3, Published Oct. 3, 1999.*

(Continued)

*Primary Examiner* — Tahmina Ansari
(74) *Attorney, Agent, or Firm* — Dority & Manning, P.A.

(57) ABSTRACT

Methods are provided for evaluating the ability of a tire to release materials from its tread during rotation. A tire tread is rotated about an axis while images of the tread are recorded to capture the effect of centrifugal forces on materials that have been loaded into the tread. The images are then used to quantify the location of certain events during the rotation of the tire tread such as when e.g., materials first began releasing from the tread during rotation and/or the rate of such release. These events can be correlated with other variables such as the rpm, centrifugal acceleration, and/or time at which such events occurred. By comparing these quantitative results for different tread patterns, the effect of differences between tread patterns can be evaluated to develop and improve the self-cleaning ability of a tire.

17 Claims, 6 Drawing Sheets

(56) References Cited

U.S. PATENT DOCUMENTS

| | | | |
|---|---|---|---|
| 3,930,141 A * | 12/1975 | Koyama et al. | 382/104 |
| 5,016,696 A | 5/1991 | Bonko et al. | |
| 5,054,918 A | 10/1991 | Downing | |
| 5,357,799 A * | 10/1994 | Roth et al. | 73/146 |
| 5,777,219 A * | 7/1998 | Popio et al. | 73/146 |
| 6,189,586 B1 | 2/2001 | Guidry | |
| 6,536,490 B2 | 3/2003 | Rooney | |
| 6,986,372 B2 | 1/2006 | Below | |
| 2005/0257609 A1* | 11/2005 | Mancosu et al. | 73/146 |
| 2007/0156320 A1* | 7/2007 | Breed et al. | 701/70 |
| 2012/0263354 A1* | 10/2012 | Berger et al. | 382/107 |

OTHER PUBLICATIONS

PCT International Search Report for PCT/US2009/065853, dated Sep. 3, 2010.*

Wei, C. Z.; Zhou, W.; Wang, Q.; Xinxin Li, "Monolithic pressure+acceleration sensor with self-test function for reliable & low-cost tire-pressure-monitoring-system (TPMS) applications," Solid-State Sensors, Actuators and Microsystems Conference (Transducers), 2011 16th International , vol., no., pp. 1006,1009, Jun. 5-9, 2011 doi: 10.1109/Transducers.*

* cited by examiner

METHOD FOR EVALUATING TIRE SELF-CLEANING CAPABILITY BY ANALYZING RECORDED IMAGES

FIELD OF THE INVENTION

The present invention relates to a method of analyzing recorded images of materials being released from a tire tread as the loaded tread experiences centrifugal forces. More particularly, the present invention provides for analyzing recorded images of treads loaded with mud or other materials while such treads are rotated to determine the effect of different tread patterns and/or tread features on the retention of such materials.

BACKGROUND OF THE INVENTION

While many road surfaces are constructed from hardened surfaces such as asphalt or concrete, tires are also frequently used in "off road" applications such as mud, gravel, sand, compacted soil, and other surfaces where the material of the surface can become loaded into the tread pattern. For example, mud can fill part or all of the grooves or other features of a tread pattern as the tire rotates during use. As the grooves or other features fill and the tire becomes loaded with mud, traction can be adversely affected as the effective tire surface becomes slick. In such case, the vehicle may become immobile or stuck. However, if the tire can self-clean or remove these materials during rotation, then the tread features have an opportunity to provide traction and thereby move the vehicle. In an ideal tire construction, during each rotation the non-contacting portions of the tread would release materials before rotating back into contact with the ground or road surface.

In addition to providing ornamental features attractive to the buyer, tread patterns may be developed for the purpose of improving traction in off road applications such as those mentioned above. In order to explore the self-cleaning efficacy of a proposed tread pattern, one or more tires can be constructed bearing the proposed pattern. In turn, these tires can then be placed on a test vehicle and subjected to various off road conditions in order to evaluate traction performance. Unfortunately, such an approach is expensive because e.g., a tire mold must be created or modified for each pattern change, the new tire must be manufactured, and then vehicle testing must be performed in off road conditions.

Figure 2:
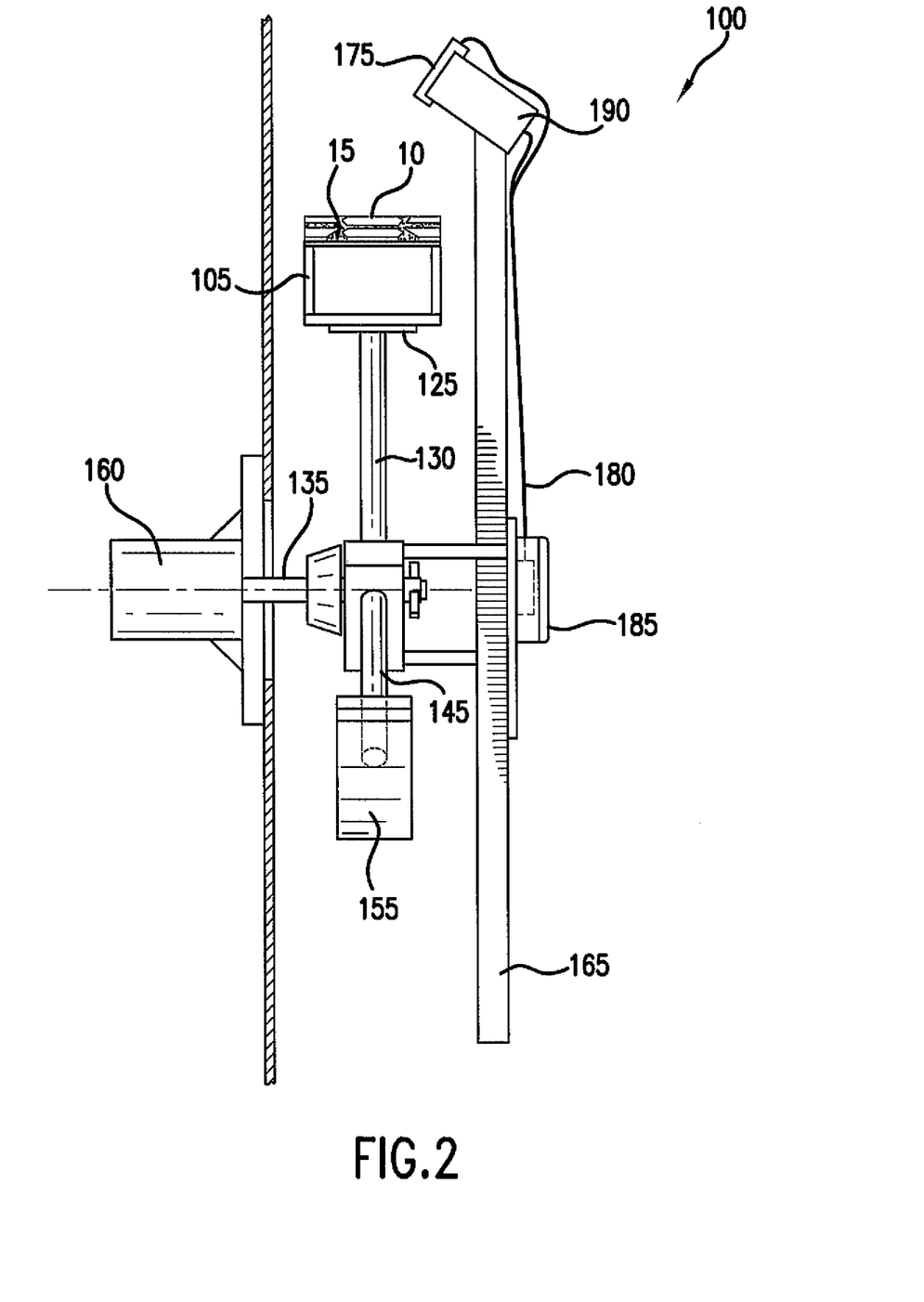
FIG. 2 illustrates a side view of the exemplary embodiment of FIG. 1.
Figure 3:
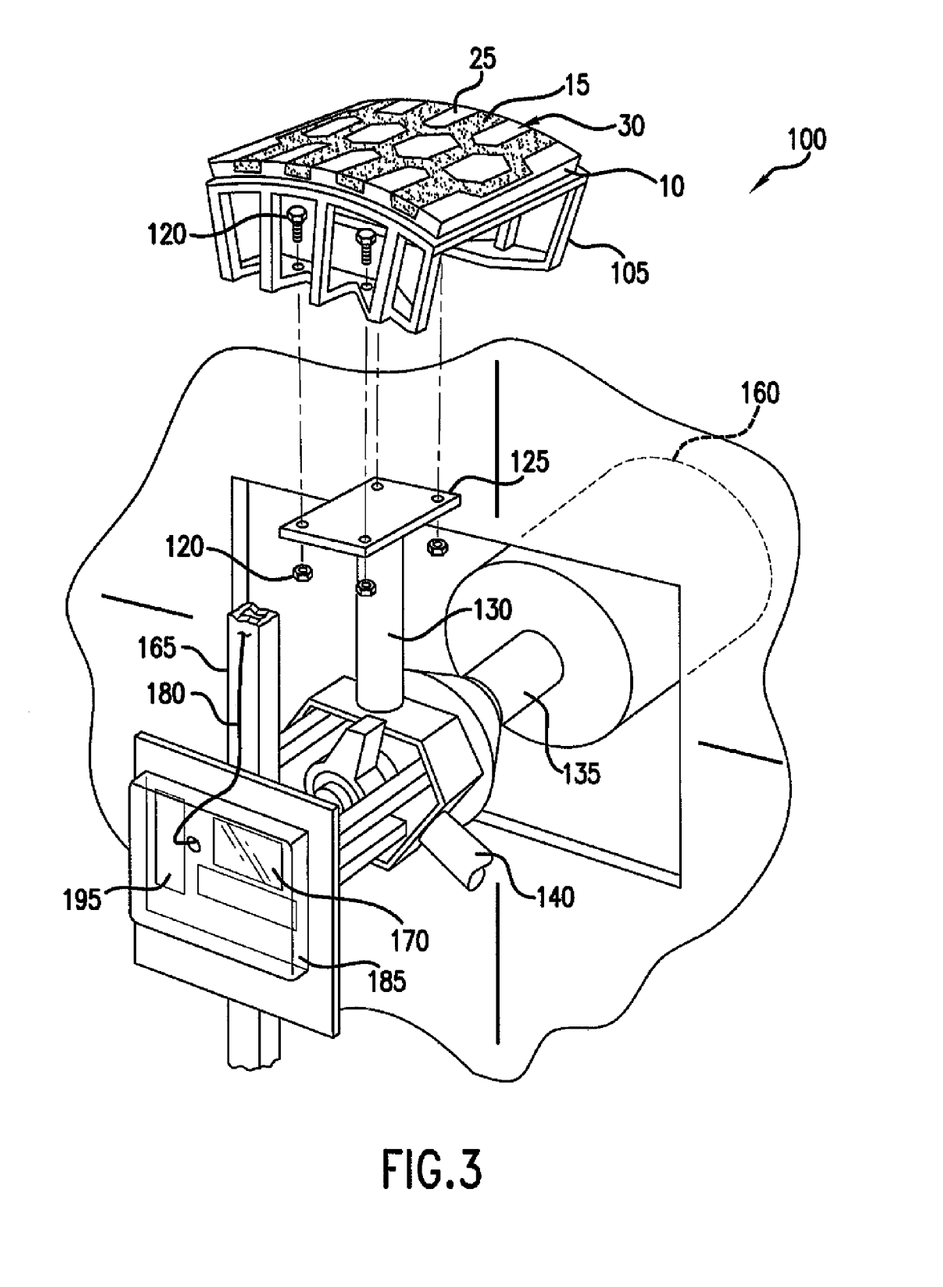
FIG. 3 is a partial perspective view of the embodiment of FIG. 1 illustrating the positioning of a tread sample portion upon the mount of the apparatus.
Figure 4:
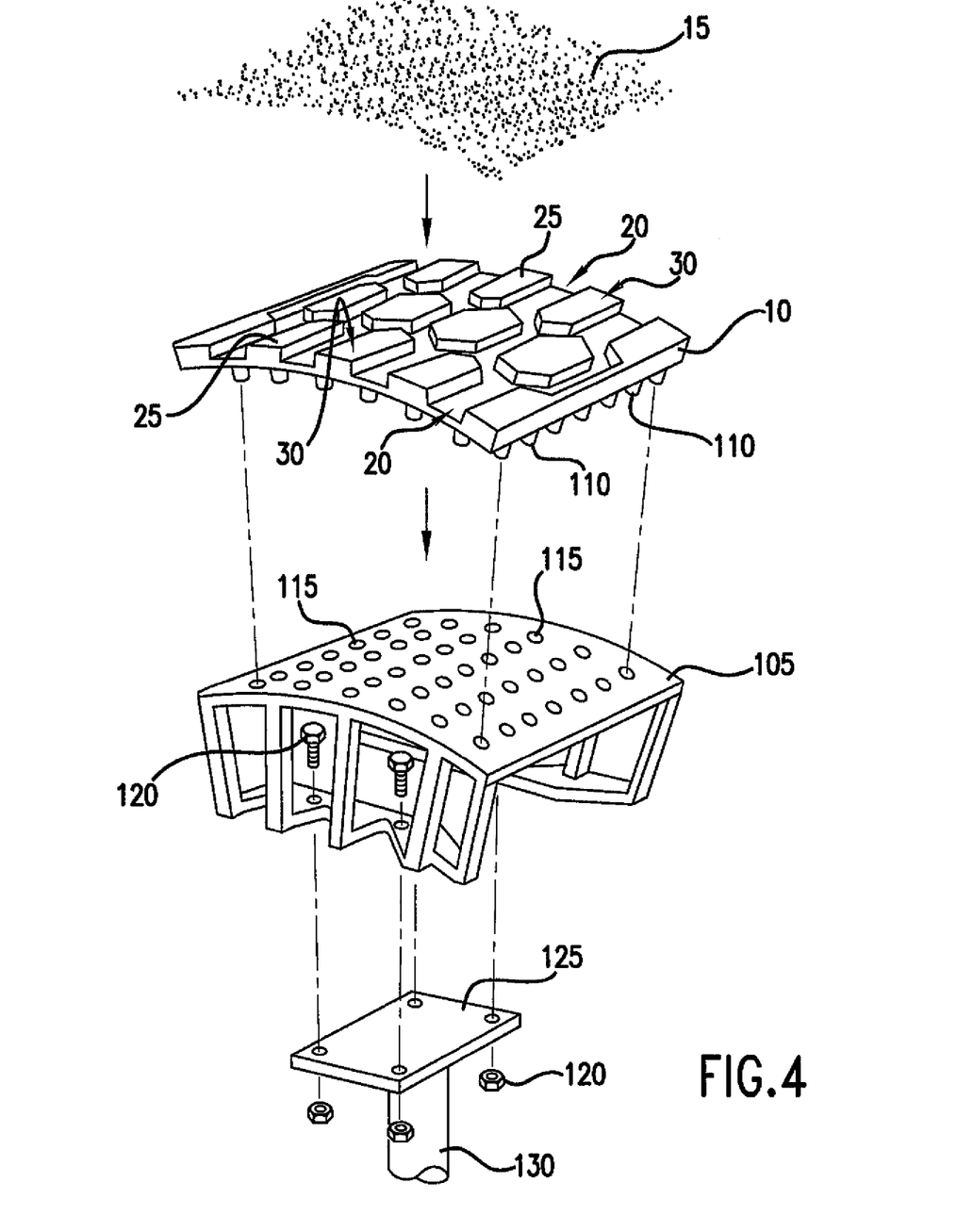
FIG. 4 illustrates the loading of a sample with materials and the mounting of the sample onto the mount.

FIGS. 1-4 illustrate an alternative where testing can be performed with just a portion of the tire tread. More specifically, apparatus 100 of FIGS. 1-4 provides an exemplary embodiment of a device that may be used to test the self-cleaning ability of a tire tread pattern, which is also described in a copending application owned by applicants' assignee. Apparatus 100 allows for testing only a portion of the tread pattern without the necessity of manufacturing the actual tire replete with tread. For example, FIG. 4 depicts a tread sample 10, which provides a portion of a tread pattern for which evaluation of the pattern's ability to self clean is desired. Sample 10 may, for example, represent one pitch of a proposed tread pattern. Sample 10 may contain a completely new pattern or may include modifications of an existing pattern for which improvements in traction are being targeted. Larger or smaller portions of the overall tread pattern may also be used for testing with apparatus 100.

Figure 1:
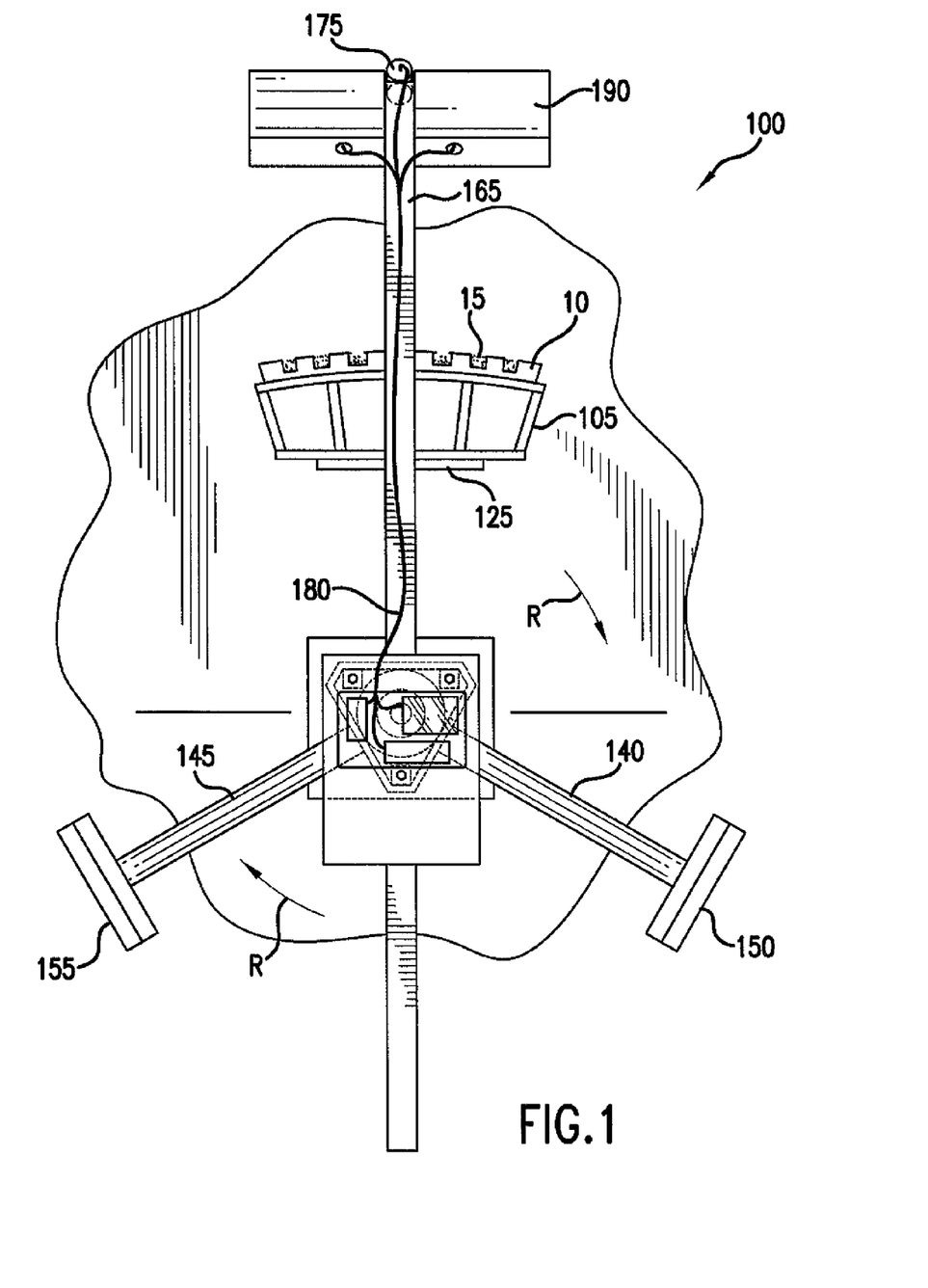
FIG. 1 illustrates a perspective view of the front of an exemplary embodiment of an apparatus that may be used to provide recorded images for analysis with the present invention so as to evaluate the self cleaning ability of a tread.

Sample 10 is loaded into a carriage 105 of apparatus 100. A plurality of pegs 110 on the non-tread side of sample 10 connect into multiple apertures 115 defined by carriage 105. Using fasteners 120, carriage 105 is attached to a mount 125 on apparatus 100. Sample 10 is loaded with materials 15. More particularly, as best shown in FIGS. 3 and 4, the grooves 20 in tread sample 10 are filled with materials 15 intended to be representative of the conditions a tire might encounter in off road operation. A variety of materials 15 may be used for testing. For example, materials such as clay, sand, and or silt may be combined with water to create a paste or "mud" that is loaded into the grooves 20 of tread sample 10.

Referring now to FIGS. 1 through 3, mount 125 is attached to an arm 130 carried upon a shaft 135 along with arms 140 and 145. Weights 150 and 155 are carried by arms 140 and 145 and counter the weight of tread sample 10, carriage 105, and mount 125 so that rotation as indicated by arrows R will be balanced about shaft 135. Shaft 135 is driven by motor 160, the speed of which can be controlled and/or measured. More specifically, the rate of acceleration, deceleration, and speed of motor 160 can be controlled and/or measured so as to create a known amount of centrifugal acceleration of tread sample 10 and materials 15 from a known rpm profile.

As sample 10 is rotated, centrifugal forces acting upon materials 15 will cause all or part of such materials to release from the tread. Images of the rotation of sample 10 and the subsequent release of materials 15 are captured by camera 170. Housed in box 185, camera 170 is connected to a camera eye 175 by wiring harness 180. Eye 175 is positioned at the end of support member 165 and rotates in synchronization with sample 10 to record the effect of the centrifugal forces on materials 15. Camera 170 may be selected from a variety of types and configurations to facilitate the recording of multiple visual images during the rotation of tread sample 10 and release of material 15. As used herein, "record" or "recording images" includes the use of a multiple different cameras and media types for visually capturing the response of materials 15 to the centrifugal forces that will be created during the rotation of sample 10. To ensure proper illumination of sample 10 and minimize the effects of other light sources during testing, apparatus 100 includes a light source 190 that also rotates in synchronization with sample 10 and camera 170. Apparatus 100 is one example of a device that may be used to provide recorded images of the release of materials 15 during the rotation of sample 10. Using the teachings disclosed herein, it will be understood that other devices could be used rotate a tire or a portion of its tread pattern and to record the release of materials such as mud from the tread.

While the recorded images provided from devices as apparatus 100 may be analyzed subjectively, the ready comparison of multiple different tread patterns using such images is difficult to accurately perform using only the raw, recorded images. More specifically, accurately determining the self-cleaning efficacy of various tread patterns and features using only the recorded images would be time consuming and subjective. A method of converting the images recorded by apparatus 100 into quantitative data for analysis and development is needed. More specifically, it would be very useful to have a method of converting the recorded images into numerical values that can be manipulated, graphically displayed, and otherwise studied for purposes of evaluating and developing tire self-cleaning ability. These and other advantages of the present invention will be apparent from the description that follows.

SUMMARY OF THE INVENTION

Objects and advantages of the invention will be set forth in part in the following description, or may be obvious from the description, or may be learned through practice of the invention.

The present invention provides a method for evaluating recorded images of materials being released from a tire tread. More specifically, the present invention provides a method of quantifying such data. For example, in one exemplary aspect, the present invention provides a method that can include the steps of rotating the tire tread about an axis; recording images of the tire tread during the rotating step; using the images from the recording step to determine when materials begin releasing from the tire tread during the rotating step; and using the images from the recording step to determine when materials stop releasing from the tire tread during the rotating step. The timing of these events, for example, provides quantitative results that may be compared with similar results for other tread patterns.

The method can also include the step of synchronizing the images with the rotational speed of the tire tread during the rotating step. This allows for determining the rotational speed or centrifugal acceleration associated with a particular image of the tire tread and, therefore, a particular event during rotation.

Various techniques can be used to further quantify the release of materials from the tread that is captured by the recording step during rotation. For example, the method can include converting the images from the recording step to black and white images and can include detecting changes in the image intensity among the black and white images. The images from the recording step can be digitized by assigning numerical values to each pixel of one or more images from the recording step. These and other steps may be employed to provide numerical values representing the release of materials form the tread pattern during the rotating step. These numerical values may be represented graphically by creating a "release profile" using the images from the recording step. The numerical values and/or release profile may be used to modify the tread pattern. Similar data may also be created using other tread patterns and compared for purposes of e.g., evaluating the efficacy of various tread patterns in releasing materials such as mud during rotation.

The images of the tire tread may be captured and recorded using a variety of different camera types to create one or more image files. In turn, these image files may be indexed to mark one or more events during the rotation of the tread sample including e.g., the beginning of tread rotation, the beginning of materials releasing from the tire tread, the ending of materials releasing from the tread, and other events as desired.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

The present invention provides a method of analyzing recorded images of materials being released from a tire tread as the loaded tread experiences centrifugal forces. More particularly, by converting images recorded from the rotation of treads loaded with mud or other materials into e.g., numerical data, the effect of different tread patterns and/or tread features on the retention of such materials can be quantitatively evaluated and developed in order to improve the self cleaning ability of a tire tread. For purposes of describing the invention, reference now will be made in detail to embodiments and/or methods of the invention, one or more examples of which are illustrated in or with the drawings. Each example is provided by way of explanation of the invention, not limitation of the invention. In fact, it will be apparent to those skilled in the art that various modifications and variations can be made in the present invention without departing from the scope or spirit of the invention. For instance, features or steps illustrated or described as part of one embodiment, can be used with another embodiment or steps to yield a still further embodiments or methods. Thus, it is intended that the present invention covers such modifications and variations as come within the scope of the appended claims and their equivalents.

As set forth above, camera 170 is used to create recorded images of the rotation of sample 10 along a predetermined rpm profile that submits materials 15 to centrifugal acceleration. Although other sequences may be used, preferably camera 170 is activated before rotation begins, remains operating during rotation, and is turned off after all materials 15 have been released or the rotation of sample 10 is stopped. In one exemplary aspect of the invention, sample 10 is rotated until all, or at least a portion, of the loaded materials 15 are released during rotation. Using camera 170, the rotation of sample 10 is recorded at least from the time rotation begins until either materials 15 are no longer releasing or rotation is ended.

Preferably, the images captured by camera 170 are stored sequentially in digital format. These images are then downloaded as one or more files onto e.g., a computer containing image processing software. Typically, these images files will be relatively large. More particularly, as stated above, generally camera 170 will be activated before rotation of sample 10 begins and remains running until after rotation stops in order to ensure that all important events are captured. This technique can create a relatively large image file that must be processed for evaluation. In order to facilitate the manipulation of such a file, a predetermined number of images (e.g., frames) are pulled or sampled from the image file to provide for the indexing or marking of certain events in the image file.

For example, every $500^{th}$ image may be pulled and reviewed to determine the general location of an event by "bracketing" such event between the pulled images. If, for example, sample 10 is not rotating at the 500th image with the image file but is seen rotating in the $1000^{th}$ image, then the start of the rotation of sample 10 took place in the bracket between the $500^{th}$ and $1000^{th}$ image in the file. Once an event has been bracketed in this manner, then the portion of the original image file that is located within the bracket may be reviewed to index (e.g., mark) the desired event and review of the entire image file (or files) is thereby avoided.

Accordingly, using this technique, at least three events are located and indexed in the image file recorded by camera 170 during the rotation of sample 10: the first image at which rotation of the sample 10 is observed, the first image at which materials 15 begin to release from sample 10 during rotation, and the first image at which materials 15 stop releasing from sample 10. In order to further conserve the computer's processing and memory capabilities, in one exemplary aspect of the present invention, subsequent processing of the image file is directed only to that portion between the beginning of rotation and the end of material release.

The precise speed (and therefore centrifugal acceleration) at any point in the image file can be determined by synchronizing the known or measured rpm profile with the start of rotation. For example, if the rpm profile includes a linear acceleration of sample 10 from 0 to 325 rpm over a six minute time period, the rpm at any given image can be determined by matching the start of the rpm profile with the now indexed start of rotation in the image file.

Next, the indexed image file is converted into a pure black and white (i.e., not grayscale) image file. To conserve computer resources and eliminate background noise, the region of interest for conversion into either black or white is defined to include only sample 10. More specifically, although the image file may include other portions of apparatus 100 such as arms 130 and the background where images were captured, the region for conversion is defined as only materials 15 and tread blocks 25 of sample 10 (FIG. 4).

Each image from the image file consists of a certain number of pixels that create the image. Pixels depicting the visible materials 15 in sample 10 are converted to white while pixels depicting the visible part of the tread sample 10 such as surfaces 30 are converted to black. This selection is arbitrary and e.g., materials 15 could be converted into black while the visible portions of sample 10 are converted into white. Differences in the image intensity between the start of the indexed image file (where the tread sample 10 is loaded with materials 15) and the end of the indexed image file (where all or portions of the materials 15 have been released) will assist in helping the image processing software distinguish between a pixel still having materials 15 and one that represents a location where materials 15 were released. More particularly, even a location on tread sample 10 where materials 15 have been released may still include some residue of materials 15 albeit with a different appearance than where material 15 have not been released. This difference in image intensity can be used to help the software distinguish between areas that should be assigned to black and areas that should be assigned to white.

The indexed image file is now analyzed to determine changes in the pixels from white to black that occurred during the rotation of sample 10. As will be understood from the above description, pixels that change from white to black during rotation represent a location on tread sample 10 where materials 15 were released. Because of the synchronization of the pixel changes with the rpm profile, the precise rpm at which a pixel changed state from white to black can also be determined. More importantly, the total number of pixels in the defined region of interest that change state from white to black can also be determined. Preferably, each frame of the indexed image file is analyzed to determine the amount of materials released from tread sample 10 at a given point in the rotation. Of course, a sampling of the image file could also be used to reduce the processing resources required.

The conversion of pixels can be quantified by digitizing the pixels. For example, each change from of a pixel from white to black can be assigned a value of one. Any pixel that did not change state is assigned a value of zero. By totaling the values at each point or image within the image file, numerical values can be used to represent the visual changes captured by the image file i.e., the release of materials 15 from tread sample 10. These values can be subjected to statistical study, graphical display, and other techniques for evaluating a visual data recording of the release of materials from one or more tread samples 10.

By way of example, the plots of FIGS. 5A through 5D represent the results of rotational testing and image analysis of four samples 10 with each sample having a different tread pattern. More particularly, each such figure represents a tread sample 10 having a different tread pattern that was loaded with materials 15 and subjected to centrifugal forces using apparatus 100 to rotate each sample 10. Each sample 10 was filled with materials 15 having the same composition and each sample was subjected to the same rpm profile. Each sample was tested multiple times to determine the reproducibility of the results. For example, FIG. 5A contains three "release profiles" labeled as A, B, and C. Such profiles A, B, and C, represent the results from repeating the same rotational test three times using the same tread sample 10 and, therefore, the same tread pattern.

Continuing with FIGS. 5A through 5D, the horizontal or x-axis for each plot represents the rpm of the sample, which could also be correlated with time because each sample was subjected to the same, predetermined rpm profile of a linear ramp from 0 to 325 rpm over a six minute period. The vertical or y-axis in each plot represents the material fraction remaining in a sample 10—with a value of 1 representing a fully loaded sample 10 and a value of zero representing an unloaded or substantially clean sample 10 where all or most of materials 15 have been released. Accordingly, each of labeled curves in FIGS. 5A through 5D is referred to herein as a "release profile" simply to denotes a graphical representation of the ability of the tread pattern to self clean or release materials from its tread over the rpm profile selected for a rotational test. Other values could be plotted for a release profile including e.g., material fraction vs. time or rpm, exposed tread vs. time or rpm, and other plots as well.

Ideally, a perfect tread pattern would release all materials from its tread with only a minimal centrifugal force. More particularly, the ideal tread pattern preferably would have a plot appearing as a straight line that is positioned close and parallel to the y-axis in FIGS. 5A through 5D. While such ideal results may presently be only theoretical, a tread pattern that approaches such results would be very desirable. In addition, a tread pattern modification that moves the testing results for that pattern more towards the y-axis and towards a plot that is more vertical is also desired as an improvement in self-cleaning ability.

Figure 5A:
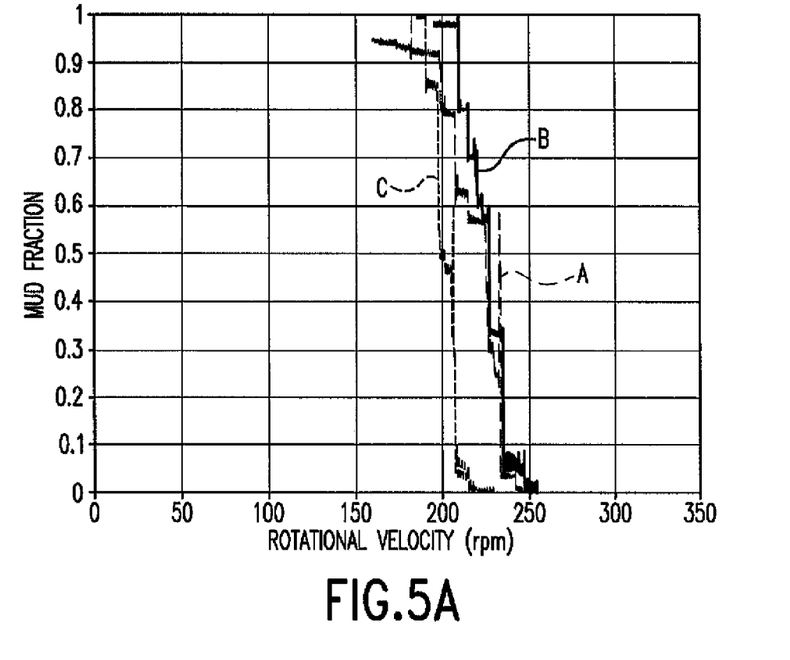
FIGS. 5A through 5D provide plots of the material release profiles for different tread patterns. Each figure represents numerical data for a different tread pattern. This numerical data was created using an exemplary method of the present invention to analyze video images of materials releasing from the tread patterns. The multiple material release profiles within each figure represent repeated tests with the same pattern.
Figure 5B:
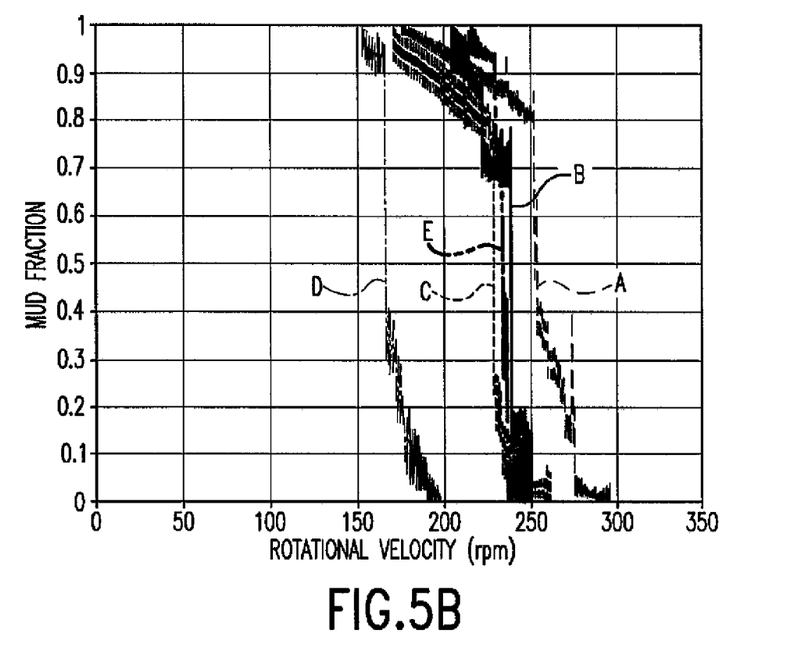
Figure 5C:
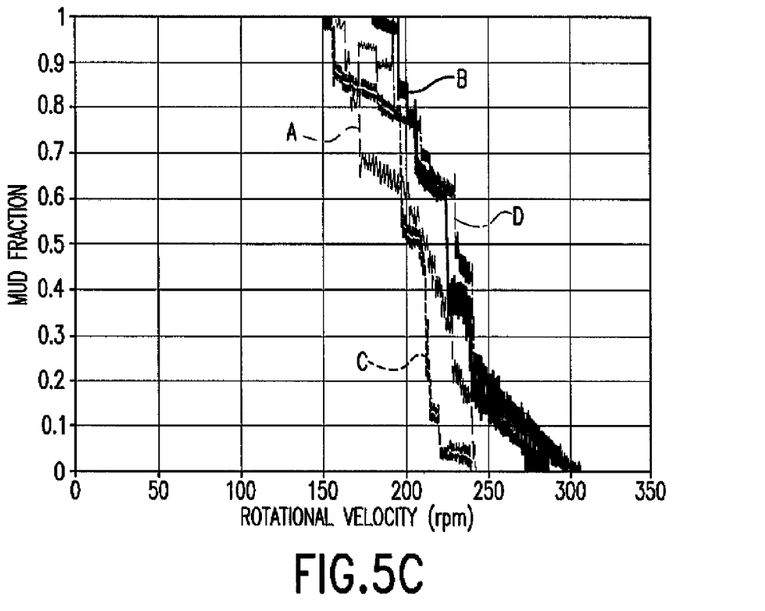
Figure 5D:
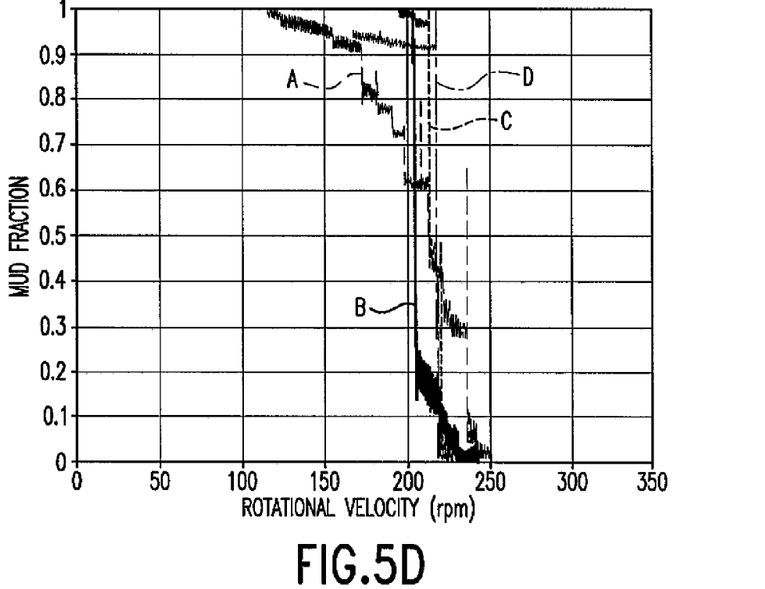

For example, referring to the release profiles, the tread pattern represented by FIG. 5C appears to require more rpm (and, therefore, more centrifugal acceleration) to release all of the materials in its tread pattern than the tread represented by FIG. 5A. Conversely, the tread pattern of FIG. 5C appears to begin releasing materials from its tread at a lower rpm than the tread represented by the release profiles in FIG. 5D.

Other approaches may also be applied for analyzing the digitized data and comparing differences in the release efficacies of various treads. For example, the rpm at which certain percentages of materials 15 have been released could be compared between various tread patterns. The points at which 25, 50 and 75 percent of all materials have been released from a tread sample could be compared between different tread patterns in order to evaluate how differences in patterns affect the ability to release materials.

Accordingly, the present invention allows for the testing and evaluation of the self-cleaning ability of new tread designs and/or modifications of tread designs. By comparing the imaging results from different patterns, the designer is provided with a guide to improving self-cleaning ability. The present invention may be used with only a portion of a tread pattern or, alternatively, images from the rotation of an existing tire loaded with materials can also be analyzed. However, when combined with apparatus 100, further economic advantages are realized in the present invention because only a portion of the tread pattern need be tested and the manufacture of a complete tire for off road testing is not necessary for each design change being considered.

Apparatus 100 is only one example of a device that may be used with the present invention to enable the capture of images during rotation of tread sample 10. Using the teachings disclosed herein, one of skill in the art will understand that other devices may be created to subject a loaded tread to centrifugal forces while allowing the capture of images for evaluation.

While the present subject matter has been described in detail with respect to specific exemplary embodiments and methods thereof, it will be appreciated that those skilled in the art, upon attaining an understanding of the foregoing, may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A method for evaluating recorded images of materials being released from a tire tread, the method comprising the steps of:
   rotating the tire tread about an axis;
   recording images of the tire tread during said rotating step;
   using the images from said recording step to determine when materials begin releasing from the tire tread during said rotating step; and
   using the images from said recording step to determine when materials stop releasing from the tire tread during said rotating step.

2. A method for evaluating recorded images of materials being released from a tire tread as in claim 1, the method further comprising the step of synchronizing the images with the rotational speed of the tire tread during said rotating step.

3. A method for evaluating recorded images of materials being released from a tire tread as in claim 1, the method further comprising the step of converting the images from said recording step to black and white images.

4. A method for evaluating recorded images of materials being released from a tire tread as in claim 3, the method further comprising the step of detecting changes in the image intensity among the black and white images.

5. A method for evaluating recorded images of materials being released from a tire tread as in claim 1, the method further comprising the step of digitizing images from said recording step by assigning numerical values to each pixel of one or more images from said recording step.

6. A method for evaluating recorded images of materials being released from a tire tread as in claim 1, the method further comprising the step of creating a release profile using the images from said recording step.

7. A method for evaluating recorded images of materials being released from a tire tread as in claim 6, the method further comprising the step of modifying the tread pattern using the results of said creating step.

8. A method for evaluating recorded images of materials being released from a tire tread as in claim 6, the method further comprising the step of comparing the results of said creating step with similar data for a different tire tread.

9. A method for evaluating recorded images of materials being released from a tire tread as in claim 1, the method further comprising the step of comparing the results of said using steps with similar data for a different tire tread.

10. A method for evaluating recorded images of materials being released from a tire tread as in claim 1, wherein said recording step further comprises creating one or more image files during said recording step.

11. A method for evaluating recorded images of materials being released from a tire tread as in claim 10, further comprising the step of indexing the image at which materials begin releasing from the tire tread.

12. A method for evaluating recorded images of materials being released from a tire tread as in claim 10, further comprising the step of indexing the image at which materials stop releasing from the tire tread.

13. A method for evaluating recorded images of materials being released from a tire tread as in claim 1, further comprising the step of determining from the images when during said rotating step a preselected percentage of the materials has been released from the tire tread.

14. A method for evaluating recorded images of materials being released from a tire tread as in claim 1, further comprising the step of using the images from said recording step to determine when said rotating step was initiated.

15. A method for evaluating recorded images of materials being released from a tire tread as in claim 1, the method further comprising the step of converting images from said recording step into numerical values representing the release or materials from the tire tread during said rotating step.

16. A method for evaluating recorded images of materials being released from a tire tread as in claim 15, the method further comprising the step of modifying the tread pattern using the results of said converting step.

17. A method for evaluating recorded images of materials being released from a tire tread as in claim 15, the method further comprising the step of comparing the results of said converting step with numerical values from rotation and recording of a different tire tread.

* * * * *